US010307099B2

(12) United States Patent
Kantor et al.

(10) Patent No.: US 10,307,099 B2
(45) Date of Patent: Jun. 4, 2019

(54) SYSTEM FOR CONTROLLED DEFIBRILLATION AND VENTILATION

(71) Applicant: INOVYTEC MEDICAL SOLUTIONS LTD, Hod Hasharon (IL)

(72) Inventors: Ehud Kantor, Hod Hasharon (IL); Mark Shahar, Holon (IL); Nir Barkai, Kfar Sava (IL)

(73) Assignee: Inovytec Medical Solutions Ltd., Hod Hasharon (IL)

( * ) Notice: Subject to any disclaimer, the term of this patent is extended or adjusted under 35 U.S.C. 154(b) by 509 days.

(21) Appl. No.: 15/034,329

(22) PCT Filed: Nov. 6, 2014

(86) PCT No.: PCT/IL2014/050969
§ 371 (c)(1),
(2) Date: May 4, 2016

(87) PCT Pub. No.: WO2015/068164
PCT Pub. Date: May 14, 2015

(65) Prior Publication Data
US 2016/0296167 A1    Oct. 13, 2016

(30) Foreign Application Priority Data

Nov. 11, 2013    (IL) .......................... 229394

(51) Int. Cl.
*A61B 5/00*    (2006.01)
*A61N 1/39*    (2006.01)
(Continued)

(52) U.S. Cl.
CPC .......... *A61B 5/4836* (2013.01); *A61B 5/0205* (2013.01); *A61B 5/0402* (2013.01);
(Continued)

(58) Field of Classification Search
CPC .... A61N 1/39; A61N 1/3904; A61N 1/39044; A61N 1/39046; A61N 1/3993; A61M 16/0051
See application file for complete search history.

(56) References Cited

U.S. PATENT DOCUMENTS

| 5,289,824 A | 3/1994 | Mills et al. |
| 2004/0016251 A1 | 1/2004 | Street et al. |

(Continued)

FOREIGN PATENT DOCUMENTS

| CN | 87213660 U | 6/1988 |
| WO | 00/51663 A2 | 9/2000 |

(Continued)

OTHER PUBLICATIONS

International Search Report for a counterpart foreign application—PCT/IL2014/050969—7 pages, dated Feb. 26, 2015.

(Continued)

*Primary Examiner* — LaToya M Louis
(74) *Attorney, Agent, or Firm* — Roach Brown McCarthy & Gruber, P.C.; Kevin D. McCarthy

(57) ABSTRACT

A system for providing decision-assisted critical care to a patient in medical emergency situations in an out of hospital setting includes: a ventilator; an Automated External Defibrillator that includes primary electrocardiogram (ECG) sensors configured as chest pads that can be connected to the chest of the patient and to sense ECG and to deliver an electric shock to the patient's heart; at least one secondary ECG sensor connected at a location other than the chest configured to sense ECG but not to deliver electric shock; and a controller configured, upon detection of shockable cardiac arrhythmias by at least one of said at least one secondary ECG sensors, to (a) instruct a caregiver to place the chest pads on the chest of the patient and to activate the (Continued)

AED, or (b) to automatically activate the AED if the chest pads are already in place on the chest of the patient.

7 Claims, 3 Drawing Sheets

(51) Int. Cl.
| | |
|---|---|
| *A61B 5/08* | (2006.01) |
| *A61B 5/0205* | (2006.01) |
| *A61B 5/0404* | (2006.01) |
| *A61B 5/0402* | (2006.01) |
| *A61B 5/145* | (2006.01) |
| *A61M 16/00* | (2006.01) |
| *A61M 16/04* | (2006.01) |
| *A61M 16/06* | (2006.01) |
| *A61H 31/00* | (2006.01) |
| *A61M 16/12* | (2006.01) |

(52) U.S. Cl.
CPC ............ *A61B 5/0404* (2013.01); *A61B 5/08* (2013.01); *A61B 5/14542* (2013.01); *A61M 16/0051* (2013.01); *A61M 16/0057* (2013.01); *A61M 16/024* (2017.08); *A61M 16/04* (2013.01); *A61M 16/06* (2013.01); *A61N 1/39* (2013.01); *A61N 1/3975* (2013.01); *A61N 1/3993* (2013.01); *A61B 5/082* (2013.01); *A61H 31/005* (2013.01); *A61H 2230/04* (2013.01); *A61H 2230/207* (2013.01); *A61H 2230/40* (2013.01); *A61H 2230/50* (2013.01); *A61M 16/125* (2014.02); *A61M 2202/0208* (2013.01); *A61M 2205/05* (2013.01); *A61M 2230/005* (2013.01); *A61M 2230/04* (2013.01)

(56) References Cited

U.S. PATENT DOCUMENTS

| | | | |
|---|---|---|---|
| 2005/0085799 | A1 | 4/2005 | Luria et al. |
| 2010/0114218 | A1 | 5/2010 | Heath |
| 2011/0202101 | A1 | 8/2011 | Tan et al. |
| 2014/0221766 | A1* | 8/2014 | Kinast .................. A61B 5/0402 600/300 |
| 2016/0015990 | A1* | 1/2016 | Helfenbein ............. A61N 1/39 600/523 |

FOREIGN PATENT DOCUMENTS

| | | |
|---|---|---|
| WO | 2004/093979 A1 | 11/2004 |
| WO | 2010/059049 A2 | 5/2010 |
| WO | 2011/004371 A1 | 1/2011 |
| WO | 2013/155503 A1 | 10/2013 |

OTHER PUBLICATIONS

Written Opinion of the International Searching Authority for a counterpart foreign application—PCT/IL2014/050969—5 pages, dated Feb. 26, 2015.

Communication from a foreign patent office (Chinese Patent Office) in a counterpart foreign application (201480061636.5), dated Apr. 1, 2017 (7 pages) and an English translation thereof (9 pages).

* cited by examiner

SYSTEM FOR CONTROLLED DEFIBRILLATION AND VENTILATION

BACKGROUND

1. Technical Field

The present invention relates to the field of life saving equipment, and more particularly, to controlling lifesaving equipment designed for the layperson care giver.

2. Discussion of Related Art

Medical emergency situations may occur in various circumstances and affect different body functions such as: trauma injuries, central nerve system injuries (e.g. stroke with apnea), cardiac conditions (e.g. coronary artery disease or cardiac arrhythmias) respiratory conditions (e.g. pulmonary embolism and chronic obstructive lung disorder, or pulmonary spastic disease), there are also systemic conditions such as anaphylactic shock, that affect multiple body functions.

Immediate medical assistance is critical to the effectiveness of life saving treatment in emergency cases. More often than not, professional medical personnel are not present at the scene of occurrence of an emergency situation, leaving the conduct of first emergency care to a lay person bystander, who is any person physically present at the scene at the time of emergency occurrence, who is capable and willing to assist, despite the lack of professional medical qualifications. The layperson care giver is therefore dependent upon lifesaving equipment which must be ultra-user friendly, as it assumes little or no medical knowledge whatsoever of the layperson care giver.

Currently there are three ubiquitous types of critical care devices: first aid kits—including bandages and the like; an Automated External Defibrillator (AED) being a portable electronic device that applies electrical shock therapy for the treatment of cardiac arrhythmias; and oxygen therapy device for either supplying oxygen enrichment or active ventilation to a patient, depending on the patient's condition. Oxygen therapy equipment is generally not available to non-professional users.

An Automated External Defibrillator (AED) is used in cases of life threatening cardiac arrhythmias which can lead to cardiac arrest. As accepted in medical practice, shockable cardiac arrhythmias include ventricular fibrillation and pulseless ventricular tachycardia (VF/VT). In both these types of shockable cardiac arrhythmia, the heart is electrically active, but in a life-threatening, dysfunctional pattern. In ventricular tachycardia, the heart beats too fast to effectively pump blood. In ventricular fibrillation, the electrical activity of the heart is chaotic, preventing the ventricle from effectively pumping blood. The fibrillation amplitude decreases over time, and eventually reaches Asystole.

AED, like any defibrillator, is not designed to cardiovert Asystole ('flat line' patterns) as it is an unconvertible rhythm. The AED provides electrical shock to a patient in cardiac arrhythmias (VF/VT) in order to synchronize the electric activity of the heart muscles, and revive the heart.

Defibrillation therapy is quite effective if applied within a short time window of 5-8 min from the time of VF/VT incidence. Studies show a 71% survival rate in witnessed cardiac arrest in casinos or airports, where AED is readily available, and the patients were treated within three minutes. After eight minutes the survival rate drops dramatically. In emergency scenarios without AED survival rate dropped to 1 to 6%.

AEDs are now commonly installed in public sites and can be used on the scene by layperson bystanders in cases of cardiac emergency. Laws mandating AEDs in public places such as schools and gyms are being enacted around the world. Unfortunately, AEDs solve only a fraction of medical emergencies related to the uncommon occurrence of cardiac arrest. Cardiopulmonary arrest is quite a rare situation, occurring in only 97/10000 cases per year in the age range of 20-75 years, causing only 30 sudden cardiac deaths per million inhabitants every week in industrialized countries. The large majority of emergency scenarios are addressed by a second module, maintaining open airway, supplying oxygen therapy, and, if needed, CPR guidance.

Oxygen therapy can treat and save a myriad of medical situations and is applied in almost one third of emergencies, including respiratory problems, cardiac problems, injuries, stress, and panic attacks.

The chest pad ECG detectors of AED devices require exposing a person's chest, often in public places. This may be highly uncomfortable for many people, especially for women or for the elderly. Therefore it would be highly desirable to have equipment that would require attachment of chest pads of an AED device only in the fraction of emergency cases that include shockable arrhythmias requiring defibrillation.

In oxygen therapy, two main systems are utilized depending on the ability of the patient to breath. If the patient is generally breathing by himself, but experiences difficulty to breath, oxygen enrichment is applied using an oxygenation device. This device is designed to increase the percentage of oxygen in the inhaled gas mixture delivered to the patient, by adding pure oxygen (from a pressurized oxygen tank through a non-invasive face mask or low pressure enrichment nasal cannula), such that the oxygen is mixed with the inhaled air, enhancing oxygen intake and maintaining body functions. In case the patient is not breathing autonomously, a ventilator should be applied, supplying pressurized air (with or without oxygen enrichment) to the patient actively inflating his lungs (either through a non-invasive face mask, or an endotracheal tube etc.). In the context discussed herein, active ventilation and passive oxygen enrichment will be commonly referred to as ventilation.

To address a wider range of emergency scenarios, an emergency device is required to supply both AED and Oxygen therapy.

Few companies provide these two modules in one carrying case. A typical example would be a portable kit of LIFE Corporation with emergency oxygen cylinder, and an AED defibrillator. In these products, the two separate modules reside in one package while being completely separated, with no communication or physical connection between them.

Due to the complexity of differential diagnosis between the various medical emergencies, the limited scope and complexity of operation of the current equipment, the stressful nature of emergency situation and the lack of medical skills of the bystander caregiver, it is highly required to provide the public with an integrated, decision assisted critical care system for successfully managing a wide scope of emergency situations, and save human lives WIPO Patent Application No. WO2011/004371 teaches a portable resuscitation system that includes a ventilation device, vital signs tracking device and airway opening device. The system is configured to track the vital signs, analyze them and provide on-place diagnosis, guidance and feedback to the caregiver. By doing so, the layperson care giver is provided with valuable guidance as to how and when to apply the ventilation device, based on the monitored vital signs. While the aforementioned system provides guidance to a layperson care giver, it is limited to a ventilation device.

US2004/0162510 describes an apparatus for performing external chest compression and defibrillation. The apparatus is comprised of a backboard to which is attached at least one chest compression member. The control circuits and the electrodes for sensing an event requiring defibrillation and for applying the electric shock and activating the chest compression member are integrated into the backboard. Embodiments of the apparatus comprise ventilators and other sensors and devices.

US2005/0085799 and WO 2010/059049 describe apparatus that comprises components that enable a non-professional to administer emergency medical treatment including external defibrillation, ventilation, and automatic chest compression.

It is a goal of the present invention to provide a device that will further cater for the needs of layperson care giver in medical emergency conditions that required either ventilation or defibrillation or both.

It is another goal of the present invention to provide a device comprising a secondary ECG detector to monitor and alert if heart fibrillation is detected requiring attachment of chest pads of an AED device.

SUMMARY OF THE INVENTION

The invention is a system for providing decision-assisted critical care to a patient in medical emergency situations in an out of hospital setting. The system comprises:
- a ventilator comprising a pressure generator and oxygen/air delivery means;
- an Automated External Defibrillator (AED) comprising a battery and primary electrocardiogram (ECG) sensors, the primary ECG sensors are configured as chest pads that are configured to be connected to the chest of the patient and configured to both sense ECG and to deliver an electric shock to the patient's heart;
- at least one secondary ECG sensor, the secondary ECG sensors configured to sense ECG but not to deliver electric shock and configured to be connected to the body of the patient at a location other than the chest; and
- a controller, configured to activate or instruct a caregiver to activate, the AED and to place the chest pads on the chest of the patient upon detection of shockable cardiac arrhythmias by at least one of the at least one secondary ECG sensors.

In embodiments of the system of the invention the oxygen/air delivery means is selected from: a closed mask, an open mask with a reservoir, an open mask without a reservoir, and an endotracheal tube (ETT).

In embodiments of the system of the invention the secondary ECG sensors are configured to be connected to the body of the patient at a location that is readily accessible. The location is selected from: a wrist, an ankle and a neck.

Embodiments of the system of the invention comprise at least one vital signs detector. The vital signs detectors can be selected from: Pulse Ox sensors, capnographs, NIBP sensor, non-invasive blood pressure (NIPB) sensors, and a pressure sensor placed in the delivery means to verify the patient's breathing.

In embodiments of the system of the invention the controller is configured to adjust the operation of the ventilator according to readings from the at least one secondary ECG sensor.

In embodiments of the system of the invention the controller is configured to adjust the operation of the ventilator according to readings from the at least one secondary ECG sensor and readings from at least one other vital signs detector.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION

Figure 1:
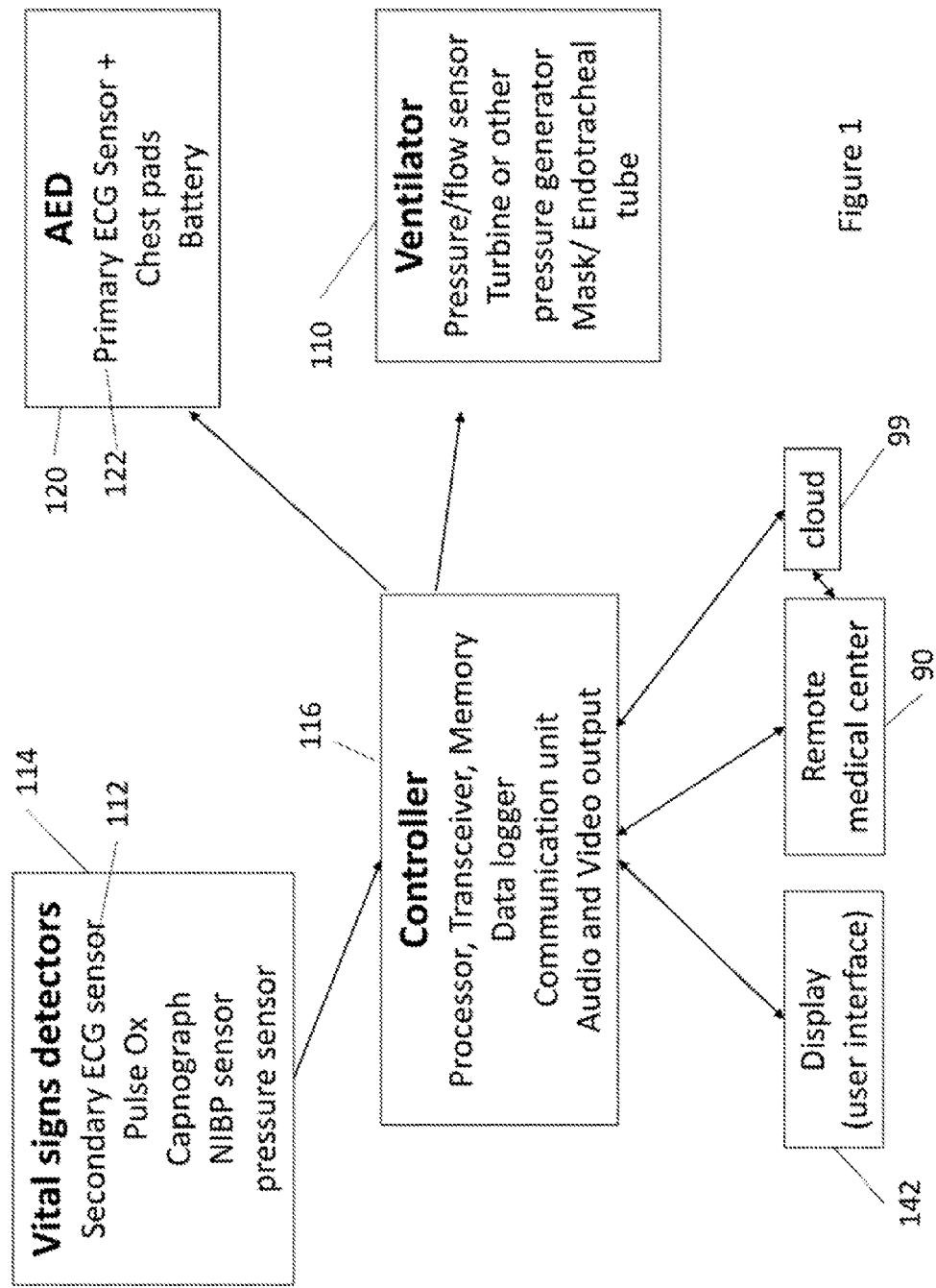
FIG. 1 is a high level schematic block diagram of defibrillation control system, according to some embodiments of the invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 is a high level schematic block diagram of system of the invention for providing critical care in medical emergency conditions. The system comprises a ventilator 110, an AED 120, a controller 116, and vital signs detectors 114.

Ventilator 110 normally comprises a pressure/flow sensor, a turbine or other pressure generator, and a delivery means to the patient such as a closed or open mask with or without a reservoir, or an endotracheal tube (ETT). The ventilator may also comprise a cylinder of pressurized oxygen or air. The ventilator may provide to the patient pure oxygen, or oxygen enrichment either passive or active, depending on the patient's condition.

AED 120 comprises a battery for generating current, chest pads 122 configured to both detect ECG signals and apply electric shock to the patient when required. Herein the chest pads 122 are also known as the primary ECG detectors.

Vital signs detector 114 may include at least one secondary ECG detector 112, designed to be attached to a readily accessible body part such as wrist, ankle or neck. The secondary ECG detectors 112 are designed to sense ECG but not to deliver an electric shock to the patient. Other vital signs detectors 114 may include PulseOx which may be placed on the patient's finger, capnograph which may be placed on the mask, and non-invasive blood pressure (NIPB) sensor, and a pressure sensor placed in the mask to verify the patients' breathing.

Controller 116 may include a processor, a transceiver, a memory unit, communication unit and an Audio/video prompting. The controller may additionally comprise a data logger to record and save the sensors readings and the entire course of events while providing critical care to a person in need. Controller 116 may also comprise a location tracking unit such as GPS, to be easily located by rescue forces.

The controller 116 is configured to receive inputs from the vital signs detectors and to adjust oxygen delivery such as flow rate and oxygen percentage according to the patient's needs. The controller 116 is configured to deliver audio/visual prompts to the user by means of display 142 (see FIG. 2), and to communicate with a remote medical center 90 via a communication link and cloud 99. The secondary ECG detectors 112 provide to the controller data on the patient's cardiac activity to enhance decision making by the controller.

Upon detection of shockable cardiac arrhythmia by at least one of the secondary ECG detectors, the controller 116 activates the AED 120, either automatically or by alerting the caregiver to turn on the AED and to place chest pads 122 on the patient's chest. The primary ECG detector 122 of the AED 120 is configured to sense and confirm the existence of cardiac shockable arrhythmia and provide guidance to the caregiver and electric shock to the patient as required. If cardiac shockable arrhythmia is not detected by the primary ECG detector 122, then the controller 116 will continue to direct the care session using information from the vital signs detectors and the ventilator 110 and guiding the caregiver through CPR if necessary.

Figure 2:
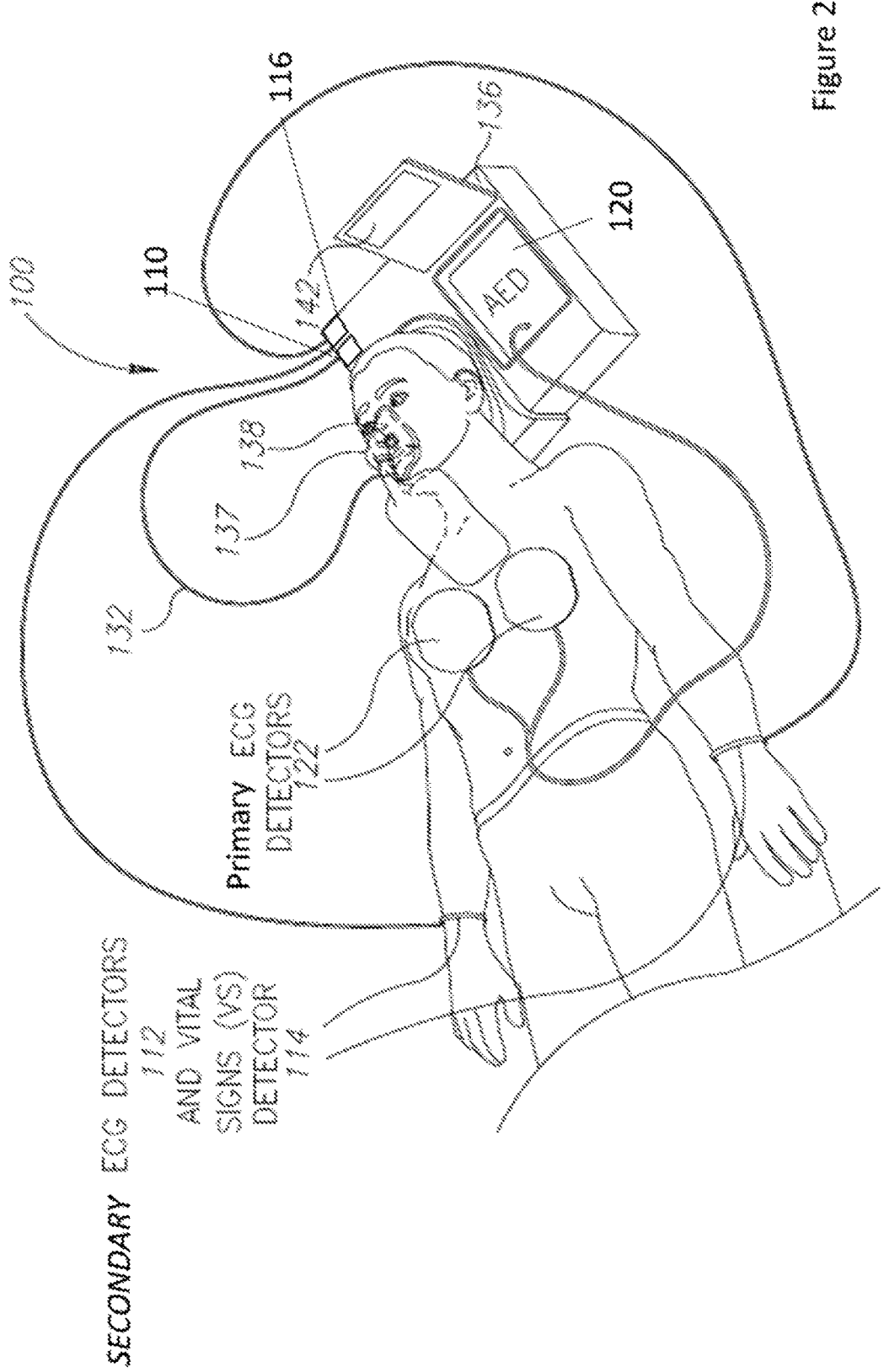
FIG. 2 is a schematic diagram illustrating a configuration of the system, according to some embodiments of the invention.

FIG. 2 is a schematic diagram illustrating a configuration of the system 100, according to an embodiment of the invention. System 100 comprises a housing 136 encompassing the ventilator 110, the AED 120, and the controller 136. FIG. 2 illustrates the system in an open configuration while treating a patient, i.e. with some of the components of the vital signs detectors 114, ventilator 110 and AED 120 attached to the patient for providing critical care. When the system is in closed configuration, i.e. when not providing critical care to a patient, the housing also encompasses the vital signs detectors, the primary ECG detectors 122, the at least one secondary ECG detector 112, face mask 137, and ventilation tube 132.

AED 120 of system 100 comprises primary ECG detectors 122, usually configured as chest pads for both sensing ECG signals and applying electrical shock to the patient if required.

Ventilator 110 of system 100 comprises a face mask 137 and a ventilation tube 132. The face mask for applying oxygen to the patient may be an open mask or a closed mask with or without a reservoir. Ventilator 110 is configured to provide oxygen enrichment or pure oxygen in a passive or active manner, for invasive or non-invasive ventilation. Embodiments of the face mask 137 comprise a respiration sensor 138, which may be positioned in a reservoir of face mask 137. Data from respiration sensor 138 may be used to determine a respiration parameter such as an inspiration/expiration ratio, a respiratory pressure rate, and respiratory volume, and may be used as one of the acquired vital signs (VS). Embodiments of other vital signs detectors, as well as the secondary ECG detectors, are configured as wrist or ankle straps, or bracelets 112.

The vital signs detectors 114 may include respiration, heart rate, temperature, blood pressure, pulse rate, and pulse oxymetry sensors to measure the corresponding vital signs of the patient. Sensors for performing such functions are well known to the ordinary skilled artisan.

A controller 116, encompassed within housing 136 of the system of the present invention is configured to activate the ventilator 110, adjust the oxygen flow to the patient based on the vital signs readings, guide the user through the care sessions via an video/audio prompter, communicate with a remote medical center, provide location data and vital signs data to the remote medical center, etc. Upon detection by at least one of the secondary ECG sensors of shockable cardiac arrhythmia (VF/VT) in the patient, the controller instructs the caregiver to expose the patient's chest, place the AED chest pads in place, and to activate the AED. Alternatively the controller may activate the AED automatically, if the chest pads 122 are already in place. If the primary ECG chest pad detectors verify the diagnosis of shockable cardiac arrhythmia the AED will apply electric shock therapy according to standard protocol.

The system 100 may also include a display 142 and a video/audio prompter to deliver messages, reading, instructions for example for applying CPR and other alerts to the caregiver. Both AED and the ventilator are able to deliver information via the controller to the user through the display 142 and embodiments of the system are adapted to allow at least some of the information to be delivered audibly to the user.

System 100 may also include an airway opening module, such as a headrest, design to tilt the head backwards in order to establish the appropriate angle between the head and neck as to establish and maintain open airway position.

In some embodiments housing 136 is designed to also function as neck support for positioning and tilting the patient's head for opening the airway. The headrest may further comprise a mechanism (not shown) for modifying a head angle of the patient in the supine position. The mechanism may comprise a motor, a servo or an inflatable bladder, and be operated manually, automatically or remotely, based on the detected VS.

Figure 3:
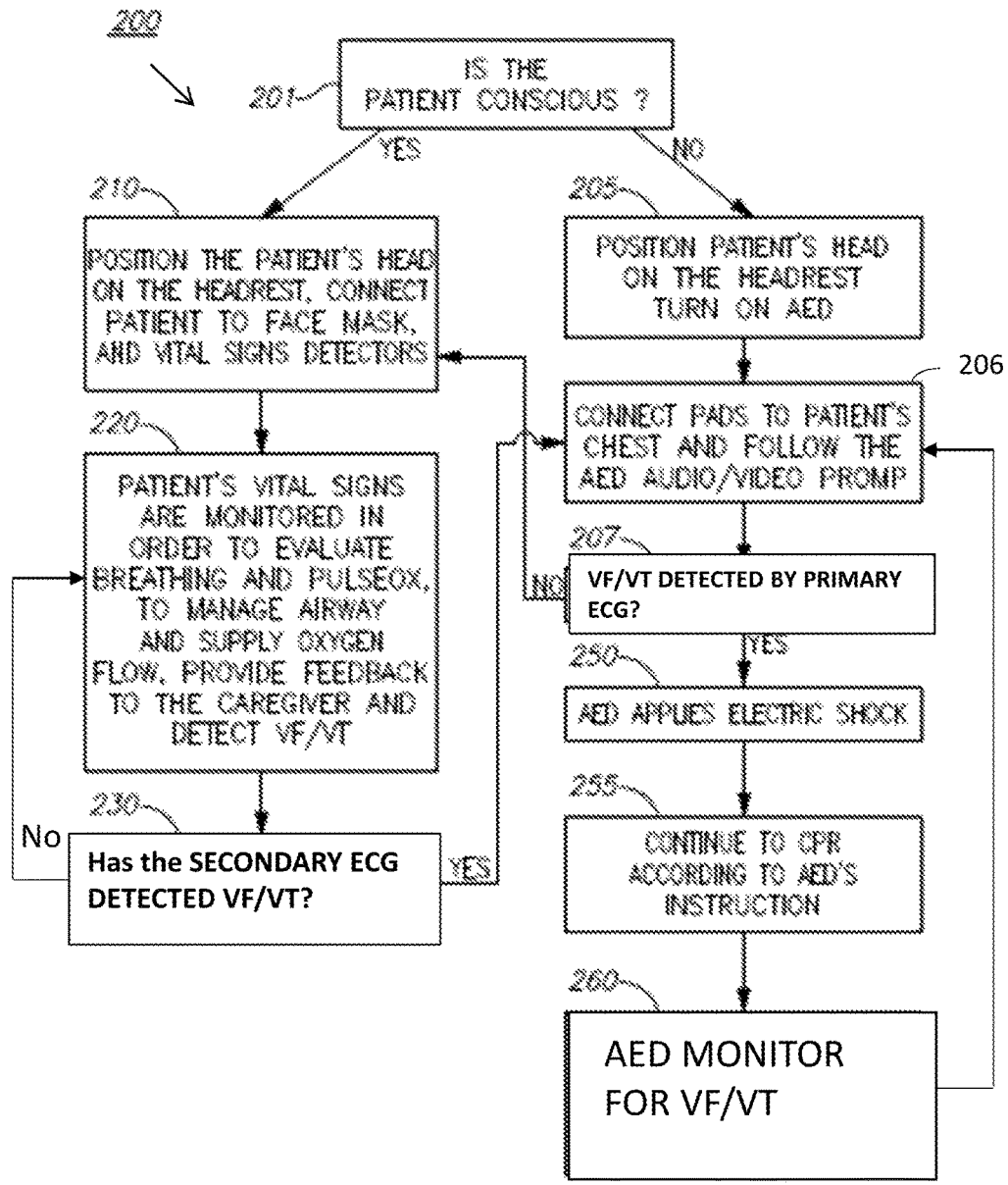
FIG. 3 is a flowchart illustrating an embodiment of the method of the invention.

FIG. 3 is a flowchart illustrating an embodiment of a method 200 for providing decision assisted critical care to a patient using the system of the invention. The method starts off with determining whether the patient is conscious (step 201). In case he is, the patient's head is positioned on the headrest and a face mask and vital signs detectors, including at least one secondary ECG sensor, are connected to the patient (Step 210). Then, the controller monitors patient's vital signs, adjusts ventilator parameters accordingly, and supplies guidance to the caregiver (step 220). In a case VF/VT is detected by at least one secondary ECG detector, the caregiver is instructed by the controller to expose the patient's chest, to attach the chest pads to the patient's chest, and to turn on the AED (step 206). In case no cardiac shockable arrhythmia (VF/VT) is detected in step 230, the method returns to step 220.

In case, in step 201, the patient is not conscious, the patient's head is positioned on the headrest and the AED is turned on (step 205). Then, the patient's chest is exposed and chest pads are connected to the chest of the patient (step 206). In case cardiac shockable arrhythmia (VF/VT) is not detected, the method goes on to step 210 described above and follows thereon. In case cardiac shockable arrhythmia (VF/VT) is detected (step 207), AED automatically applies an electric shock (step 250. After electric shock is applied using the primary ECG electrodes, the processor determines if CPR should be carried out and if so prompts the caregiver and guides him/her through the CPR procedure (step 255). If CPR is not necessary or while it is being applied the primary ECG detectors continue to monitor for VF/VT (step 260) and the method cycles back to step 207. If in step 207, at least one of the primary ECG detectors does not detect VF/VT, then the method returns to step 210

Although embodiments of the invention have been described by way of illustration, it will be understood that the invention may be carried out with many variations, modifications, and adaptations, without exceeding the scope of the claims.

The invention claimed is:

1. A system for providing decision-assisted critical care to a patient in medical emergency situations in an out of hospital setting, said system comprising:
    a ventilator comprising a pressure generator and a mask or endotracheal tube for delivering to the patient one of: (a) oxygen, (b) air, or (c) oxygen and air;
    an Automated External Defibrillator (AED) comprising a battery and primary electrocardiogram (ECG) sensors, said primary ECG sensors configured as chest pads that are configured to be connected to the chest of said patient and configured to both sense ECG and to deliver an electric shock to said patient's heart;
    at least one secondary ECG sensor, said secondary ECG sensors configured to sense ECG but not to deliver electric shock and configured to be connected to the body of said patient at a location other than the chest; and
    a controller configured, upon detection of shockable cardiac arrhythmias by at least one of said at least one secondary ECG sensors, to (a) instruct a caregiver to place said chest pads on the chest of said patient and to activate said AED, or (b) to automatically activate said AED if said chest pads are already in place on the chest of said patient;
    said system characterized in that, upon detection of shockable cardiac arrhythmia by at least one of said secondary ECG sensors, the AED is configured to: (a) in case said primary ECG sensors sense and confirm the existence of cardiac shockable arrhythmia, said AED applies electric shock therapy according to standard protocol; and (b) if said primary ECG sensors do not sense and confirm the existence of cardiac shockable arrhythmia, said AED does not apply an electric shock.

2. The system of claim 1, wherein the mask for delivering to the patient one of: (a) oxygen, (b) air, or (c) oxygen and air is selected from: a closed mask, an open mask with a reservoir, an open mask without a reservoir, and an endotracheal tube (ETT).

3. The system of claim 1, wherein the secondary ECG sensors are configured to be connected to the body of the patient at a location that is readily accessible, said location selected from: a wrist, an ankle and a neck.

4. The system of claim 1 comprising at least one vital signs detector.

5. The system of claim 4, wherein the vital signs detectors are selected from: Pulse Ox sensors, capnographs, non-invasive blood pressure sensors, and pressure sensor placed in the delivery means to verify the patient's breathing.

6. The system of claim 4, wherein the controller is configured to adjust the operation of the ventilator according to readings from the at least one secondary ECG sensor and readings from at least one other vital signs detector.

7. The system of claim 1, wherein the controller is configured to adjust the operation of the ventilator according to readings from the at least one secondary ECG sensor.

* * * * *